(12) United States Patent
Grant et al.

(10) Patent No.: US 11,197,902 B2
(45) Date of Patent: Dec. 14, 2021

(54) PREBIOTIC NEUTRACEUTICAL COMPOSITIONS AND METHODS OF TREATMENT USING THE SAME

(71) Applicant: IG Biosciences Corporation, Dubuque, IA (US)

(72) Inventors: Valentino Grant, Pembroke Pines, FL (US); Dayna J. Campbell, Pembroke Pines, FL (US); George D. Ranglin, Pembroke Pines, FL (US)

(73) Assignee: IG Biosciences Corporation, Dubuque, IA (US)

( * ) Notice: Subject to any disclaimer, the term of this patent is extended or adjusted under 35 U.S.C. 154(b) by 459 days.

(21) Appl. No.: 15/631,422

(22) Filed: Jun. 23, 2017

(65) Prior Publication Data
US 2017/0368118 A1 Dec. 28, 2017

Related U.S. Application Data

(60) Provisional application No. 62/354,287, filed on Jun. 24, 2016.

(51) Int. Cl.
| | |
|---|---|
| A61K 36/06 | (2006.01) |
| A23K 20/163 | (2016.01) |
| A23K 10/18 | (2016.01) |
| A23K 20/147 | (2016.01) |
| A23K 20/10 | (2016.01) |
| A23L 33/19 | (2016.01) |
| A23L 33/14 | (2016.01) |
| A23L 33/00 | (2016.01) |
| A23L 33/135 | (2016.01) |
| A61K 9/14 | (2006.01) |
| A61K 35/742 | (2015.01) |
| A61K 35/744 | (2015.01) |
| A23K 50/48 | (2016.01) |
| A61K 9/00 | (2006.01) |
| A61K 9/10 | (2006.01) |
| A61K 9/08 | (2006.01) |
| A61K 9/107 | (2006.01) |
| A23K 50/60 | (2016.01) |
| A23K 50/40 | (2016.01) |
| A61K 9/06 | (2006.01) |
| A61K 35/747 | (2015.01) |
| C07K 16/00 | (2006.01) |

(52) U.S. Cl.
CPC .............. *A61K 36/06* (2013.01); *A23K 10/18* (2016.05); *A23K 20/10* (2016.05); *A23K 20/147* (2016.05); *A23K 20/163* (2016.05); *A23K 50/40* (2016.05); *A23K 50/48* (2016.05); *A23K 50/60* (2016.05); *A23L 33/135* (2016.08); *A23L 33/14* (2016.08); *A23L 33/19* (2016.08); *A23L 33/30* (2016.08); *A23L 33/40* (2016.08); *A61K 9/0053* (2013.01); *A61K 9/0056* (2013.01); *A61K 9/0095* (2013.01); *A61K 9/06* (2013.01); *A61K 9/08* (2013.01); *A61K 9/10* (2013.01); *A61K 9/107* (2013.01); *A61K 9/14* (2013.01); *A61K 35/742* (2013.01); *A61K 35/744* (2013.01); *A61K 35/747* (2013.01); *C07K 16/00* (2013.01); *A23V 2002/00* (2013.01)

(58) Field of Classification Search
CPC ....... A61K 36/06; A23L 33/135; A23L 33/14; A23K 20/147
See application file for complete search history.

(56) References Cited

U.S. PATENT DOCUMENTS

| | | | |
|---|---|---|---|
| 6,793,921 B2 * | 9/2004 | Kodama | A61K 39/40 424/157.1 |
| 7,981,412 B2 * | 7/2011 | Gorbach | A23C 9/1307 424/93.45 |
| 2005/0037421 A1 | 2/2005 | Honda et al. | |
| 2005/0079244 A1 | 4/2005 | Giffard et al. | |
| 2007/0207187 A1 | 9/2007 | Yajima et al. | |
| 2011/0268743 A1 | 11/2011 | Benyacoub et al. | |
| 2013/0216521 A1 | 8/2013 | Culver et al. | |

FOREIGN PATENT DOCUMENTS

| | | | | |
|---|---|---|---|---|
| CN | 102641500 A | * | 8/2012 | |
| CN | 105614107 A | * | 6/2016 | |
| DE | 202013010180 U1 | * | 12/2013 | ............ A23L 33/10 |
| EP | 904784 A1 | | 3/1999 | |
| WO | 199404678 A1 | | 3/1994 | |
| WO | 2003014161 A2 | | 2/2003 | |

OTHER PUBLICATIONS

"Fast Balance GI 60cc Calibrated Tube," https://www.amazon.com/VetriScience-Laboratories-Fast-Balance-Calibrated/dp/B0009UD0BC, accessed on Jun. 13, 2017.

(Continued)

*Primary Examiner* — Amy L Clark

(74) *Attorney, Agent, or Firm* — McKee, Voorhees & Sease, PLC

(57) ABSTRACT

Methods for treatment and compositions are provided for increasing the health of humans, livestock, and companion animals. More particularly, dietary supplements (also referred to as PPA (prebiotic, probiotic, antibodies) compositions) for treating humans, livestock, and companion animals, and methods for making and using them for treatment of various conditions are disclosed.

5 Claims, No Drawings

(56) References Cited

OTHER PUBLICATIONS

"FADPX Egg Proteins and Probiotics," http://agrilac.com/index. php/component/virtuemart/404/egg-powder-gives-calves-a-boost/fadpx-egg-proteins-and-probiotics-detail?Itemid=64, accessed on Jun. 13, 2017.
"Fast Balance GI for Dogs, Cats & Horses by Vetriscience," http://www.vetriscience.com, accessed on Jun. 13, 2017.
"Probiotics for Dogs and Cats, Probiotics May Helt Support Your Pet's GI Tract," https://www.proplanveterinarydiets.com/probiotics, 6 pages, accessed on Jun. 13, 2017.
"Proviable-Forte Digestive Health Supplement for Dogs & Cats," http://www.proviable.com/Proviable-Forte.html, accessed on Jun. 13, 2017.
"Purina FortiFlora," http://www.1800petmeds.com/Purina+FortiFlora-prod10376.html, accessed on Jun. 13, 2017.
IG Biosciences Corporation, PCT/US17/38961 filed Jun. 23, 2017, "Notification of Transmittal of the International Search Report and the Written Opinion of the International Searching Authority, or the Declaration", dated Sep. 13, 2017.

* cited by examiner

PREBIOTIC NEUTRACEUTICAL COMPOSITIONS AND METHODS OF TREATMENT USING THE SAME

CROSS-REFERENCE TO RELATED APPLICATIONS

This application claims priority and is related to U.S. Provisional Application Ser. No. 62/354,287 filed on Jun. 24, 2016 and entitled Prebiotic Neutraceutical. The entire contents of this patent application are hereby expressly incorporated herein by reference including, without limitation, the specification, claims, and abstract, as well as any figures, tables, or drawings thereof.

FIELD OF THE INVENTION

The present invention relates to the methods and compositions for increasing the health of humans, livestock, and companion animals. More particularly, the present invention relates to dietary supplements (also referred to as prebiotic neutraceutical compositions or PPA (prebiotic, probiotic, antibodies) compositions) for treating humans, livestock, and companion animals, and methods for making and using them for treatment of various conditions.

BACKGROUND OF THE INVENTION

Animals, including humans, are consistently at risk of contracting infections from microorganisms, including bacteria, viruses, protozoa, and helminths. While a number of innate and adaptive immune responses exist, the stimulation and strengthening of these responses can lead to a reduction in diseases and infections. Such stimulation can be achieved through a dietary supplement which provides components that increases the natural defensive responses. In particular, such dietary supplements for animals often target diseases and infections which spread through the digestive system. Such diseases and infections include but are not limited to, for example, pharyngeal paralysis, enteric camplyobacteriosis, salmonellosis, Tyzzer disease, amebiasis, coccodiosis, cryptosporidiosis, giardiasis, colic, bovine viral diarrhea, jejunal hemorrhage syndrome, dysentery, necrotic enteritis, intestinal adenocarcinoma, Potomac horse fever, entercololitis, colitis-X, coronavirus, parasites, *Clostridium difficile* enteritis, *Clostridium perfringens* enteritis, hemorrhagic bowel syndrome, porcine proliferative enteritis, rotaviral enteritis, transmissible gastroenteritis, *Fasciola hepatica, Fasciola gigantic, Fascioloides magna, Dicrocoelium dendriticum, Eurytrema* ssp, paramphistomes, parvovirus, feline enteric coronavirus, gastric dilation and volvulus, *Helicobacter* infection, and gastritis.

The presence of such diseases and/or infections in livestock can affect herd health and animal performance, including feed intake, feed efficiency, production of milk, meat, or other animal products, and maintaining acceptable levels of milk components. An overall high level of herd health reduces the risk and incidence of disease and infection. Current practices of maintaining herd health and treating disease and infection often include treatment via antibiotics and vaccines, however, in some instances treatment must occur within hours of detection in order to prevent a widespread outbreak or loss of the animal. Additionally, in light of a growing market for animal products produced without the use of antibiotics or vaccines, disease and infection prevention is critical. In the instance of companion animals, the prevention of diseases and infections passed through the digestive system lessens the risk of contracting a highly contagious disease during day-to-day activities. In humans, these diseases are responsible for significant morbidity, and contribute to the increasing costs of healthcare.

Various probiotic and prebiotic compositions are commercially available for animal use, namely including veterinarian-prescribed products. Various prebiotics and/or probiotic strains are employed to support health of animals, namely intestinal health. However, there remain limitations and shortcomings of these commercially-available formulations. Moreover, their singular use is unable to adequately treat and prevent various diseases and conditions.

A number of diseases and conditions in humans, livestock, and companion animals do not have effective treatments. For example, inflammatory bowel disease (IBD) lack effective treatment and prevention options. In addition, while specific treatment or prevention options may be available for particular diseases or conditions, there is a lack of broad spectrum treatments that are effective against several important pathogens, infections, diseases, and/or conditions. There is therefore a need for compositions that are effective in preventing or treating a variety of infections, diseases, and/or conditions in animals, including humans.

Thus, it is an aim of the present invention to provide dietary supplements (also referred to as PPA neutraceutical compositions) for treatment and/or prevention of various conditions in humans, livestock, and companion animals.

It is a further aim of the present invention to stimulate immune and digestive health in order to prevent disease and infection by providing a dietary supplement which provides improved availability of healthy gut flora. Other objects, advantages and features of the present invention will become apparent from the following specification.

BRIEF SUMMARY OF THE INVENTION

The present invention provides compositions and methods for treatment and prevention of disease and conditions. The invention further provides methods for producing such compositions. In one aspect, the compositions include an immune effector protein component, a prebiotic component (also referred to herein as a prebiotic), and a probiotic component. In a further aspect, the composition may be a dietary supplement.

In a further aspect, the dietary supplement compositions may include a prebiotic yeast component and an immune effector protein component, a prebiotic yeast component and a probiotic component; an immune effector protein component and a probiotic component; an immune effector protein component, a prebiotic component, and a probiotic component; or a prebiotic yeast component, an immune effector protein component, and a probiotic component.

In another aspect, the invention provides methods of treating an infection or disease in an animal by providing an animal with a composition including the prebiotic yeast component, an immune effector protein component, and a probiotic component. In a further aspect, the method can involve providing such a composition as a liquid or suspension or as a solid food additive.

In another aspect, the present invention provides methods of improving the health of an animal comprise providing an animal with a composition comprising a prebiotic yeast component, an immune effector protein component, and a probiotic component.

The invention further provides methods of producing compositions for treating diseases or conditions, comprising combining one or more, or preferably two or more of a prebiotic yeast component, an immune effector protein component, and a probiotic component. The production can involve producing a liquid or suspension or a solid composition.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE INVENTION

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. The methods and techniques are generally performed according to conventional methods well known in the art and as described in various general and more specific references that are cited and discussed throughout the present specification unless otherwise indicated. The following definitions and introductory matters are provided to facilitate an understanding of the present invention.

Numeric ranges recited within the specification, including ranges of "greater than," "at least," or "less than" a numeric value, are inclusive of the numbers defining the range and include each integer within the defined range. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The term "animal" as used herein includes, but is not limited to, humans, companion animals, and livestock. The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

term "companion animal" refers to domesticated animals raised for human companionship purposes and include birds, cats, dogs, and small mammals such as, for example, rabbits and rodents.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life. As used herein, an "effective amount" refers to the amount of component and/or the PPA neutraceutical compositions of the invention that is sufficient to prevent, treat, reduce and/or ameliorate the symptoms and/or underlying causes of a disorder or disease.

The term "gut" refers to the gastrointestinal tract as well as liver, spleen, pancreas, omentum, and other organs served by the blood supply to and from the gut.

The terms "include" and "including" when used in reference to a list of materials refer to but are not limited to the materials so listed.

"Mammals" include any warm-blooded vertebrates of the Mammalia class, including humans. The term "ungulate" refers to any mammal with hooves including odd-toed ungulates such as horses and even-toed ungulates such as cattle and pigs. In the context of the present invention the term "ungulate" excludes cetaceans such as whales or dolphins. The term "microorganism" refers to an organism or microbe of microscopic, submicroscopic, or ultramicroscopic size that typically consists of a single cell. Examples of microorganisms include bacteria, viruses, parasites, fungi, certain algae, and protozoa. The term "microbial" indicates pertaining to, or characteristic of a microorganism.

The term "livestock" refers to domesticated animals raised for a commercial purpose, such as food, fiber and labor. Such animals may include cattle, swine, lambs, goats, poultry, and equine.

The terms "porcine" and "swine" are used interchangeably herein and refer to any animal that is a member of the family Suidae such as, for example, a pig.

The term "subject" or "patient" as used herein means all mammals including humans. Non-limiting examples of subjects include humans, cows, dogs, cats, horses, goats, sheep, pigs, and rabbits.

As used herein, reference to "treatment" of a subject or patient is intended to include prevention, prophylaxis and therapy.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

In one aspect, the present invention involves dietary supplement and PPA neutraceutical compositions for treatment and prevention of disease. The compositions can comprise a combination of two or more, or three or more components, where the components are: a prebiotic hydrolysed yeast or yeast-based extract; an immune effector protein; and a probiotic. In a preferred embodiment the compositions comprise all three components.

A composition can be formulated to be compatible with its intended route of administration. Examples of routes of administration for components of the present invention include oral, buccal, injectable, intravenous, intraperitoneal, subcutaneous, inhalational, intramuscular, intraarticular, intraarterial, intracerebral, intracerebellar, intrabronchial, intrathecal, parenteral, rectal, sublingual, topical, transdermal, and aerosol route. Oral compositions are preferred according to an embodiment of the invention and generally include an inert diluent or an edible carrier. They can be enclosed in gelatin capsules, caplets compressed into tablets, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, gummie, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, yogurts, cereal coatings, foods, nutritive foods, and combinations thereof.

The compositions can be in solid or liquid form, and may be incorporated into a food source or water source. Liquid forms can include for example solutions, suspensions and/or emulsions. Solid forms can include for example powders and/or pastes. Alternatively, the compositions may be formulated for use as a gavage composition. As referred to herein the gavage composition refers to a composition suitable for administering through a feeding tube.

In one aspect, the compositions can be administered alone or formulated with pharmaceutically acceptable compounds known in the art, vehicles, or adjuvants with a favorable delivery profile, i.e., suitable for delivery to a subject. A "pharmaceutically acceptable carrier" can include any solvent(s), dispersion media, coatings, antibacterial and antifungal compounds, isotonic and absorption delaying compounds that are compatible with pharmaceutical administration. In one aspect, the components of the compositions can be mixed in equal proportions. For example, in compositions comprising two components, the two components can be present in a 1:1 ratio. In compositions comprising three components, the three components can be present in a 1:1:1 ratio. In another aspect, the components can be present in unequal proportions. For example, in compositions comprising two components, the two components can be present in ratios between 10:1 and 1:10, including all ratios in between. In compositions comprising three components, the components can be present in ratios of the prebiotic to the immune effector protein to the probiotic ranging from 1:1:10-1:10:10-10:10:1-10:1:1 and all ratios in between.

Immune Effector Proteins

In one aspect, the compositions of the present invention may comprise an immune effector protein component. The immune effector protein component may include one or more of antibodies or immunoglobulins, functional fragments thereof, and antibody analogues. As used herein, the term "antibody molecule" refers to an antibody, antibody peptide(s) or immunoglobulin, or an antigen binding fragment of any of the foregoing, e.g., of an antibody. Antibody molecules include single chain antibody molecules, e.g., scFv, see. e.g., Bird et al. (1988) Science 242:423-426; and Huston et al. (1988) Proc. Natl. Acad. Sci. USA 85:5879-5883), and single domain antibody molecules, see, e.g., WO9404678. Although not within the term "antibody molecules," the invention also includes "antibody analog(s)," other non-antibody molecule protein-based scaffolds, e.g., fusion proteins and/or immunoconjugates that use CDRs to provide specific antigen binding.

As used herein, the term "antibody," "antibody peptide(s)" or "immunoglobulin" refers to single chain, two-chain, and multi-chain proteins and glycoproteins. The term antibody includes polyclonal, monoclonal, chimeric, CDR-grafted and human or humanized antibodies. Also included within the term are camelid antibodies, see, e.g., US2005/0037421, and nanobodies, e.g., IgNARs (shark antibodies), see, e.g., WO03/014161. The term "antibody" also includes synthetic and genetically engineered variants.

As used herein, the term "antibody fragment" or "antigen binding fragment" of an antibody refers, e.g., to Fab, Fab', F(ab').sub.2, and Fv fragments, single chain antibodies, functional heavy chain antibodies (nanobodies), as well as any portion of an antibody having specificity toward at least one desired epitope, that competes with the intact antibody for specific binding (e.g., a fragment having sufficient CDR sequences and having sufficient framework sequences so as to bind specifically to an epitope). E.g., an antigen binding fragment can compete for binding to an epitope which binds the antibody from which the fragment was derived. Derived, as used in this and similar contexts, does not imply any particular method or process of derivation, but can refer merely to sequence similarity. Antigen binding fragments can be produced by recombinant techniques, or by enzymatic or chemical cleavage of an intact antibody. The term, antigen binding fragment, when used with a single chain, e.g., a heavy chain, of an antibody having a light and heavy chain means that the fragment of the chain is sufficient such that when paired with a complete variable region of the other chain, e.g., the light chain, it will allow binding of at least 25, 50, 75, 85 or 90% of that seen with the whole heavy and light variable region.

In a preferred embodiment, the immune effector component comprises IgY antibody molecules. The IgY antibodies can be specific for one or more antigens, microbes, and/or pathogens. In a further aspect, the IgY antibodies of the immune effector protein component are specific for a variety of intestinal pathogenic microbes.

The immune effector protein component can be derived from any known source. For example, the immune effector protein component can be isolated or derived from blood or blood products, such as serum or plasma. The immune effector components may also be derived or isolated from cells or cell cultures. For example, the immune effector components can comprise immunoglobulins produced and/or secreted by immortalized cells. In another aspect, the immune effector protein component can be derived from eggs.

In an exemplary embodiment, the immune effector protein component can be a commercially available product. Commercially available immune effector protein components include Globimax egg protein, produced by EW Nutrition.

In an aspect of the invention, the composition provides from about 0.1 gram to about 0.5 grams of the immune effector protein in a 1 gram dosage, or from about 0.25 grams to about 0.5 grams of the immune effector protein in a 1 gram dosage.

Prebiotic Yeast Component

In one aspect, compositions according to the present comprise a prebiotic. Prebiotics are non-digestible and non-absorbable carbohydrates introduced into the gastrointestinal (GI) tract. They stimulate the growth of beneficial microflora in the gut such as *Bifidobacterium* and *Lactobacillus* and consequently increase the production of lactic and acetic acids. This results in a decrease of the development of pathogen enterobacteria.

In one aspect, compositions according to the present may comprise a prebiotic yeast component, which may be composed of yeast cells, yeast products, yeast derivatives, or yeast-based extracts. Yeasts are unicellular, eukaryotic microorganisms. In a preferred embodiment, the prebiotic yeast components are components of the Cell Wall of the Yeast *Saccharomyces cerevisiae*. Yeast cells are composed of proteins, amino acids, carbohydrates, vitamins and minerals, as well as cell wall components, including glucans, chitin, xylose, mannose, glucuronic acid, and galactose. Yeast can be used as dietary supplements in a deactivated form to provide high levels of micro constituents including proteins, B vitamins, fats, sugars, enzymes, and other nutrients. Yeasts, yeast products, derivatives, and extracts may include any of the components, and may be enriched for particular components. In a preferred embodiment, the yeast component comprises mannan oligosaccharides, beta glucans, mannose (including D-mannose), and galactosamine. In a further aspect, yeasts, yeast products, derivatives, and extracts may include yeast cells or components of yeast cells from two or more species of yeast.

For purposes of this invention, the yeast species may be any yeast which provides the desired health benefits, for example, those in the subplyum, pezizomycotina, saccharomycotina, taphirnomycotina, pucciniomycotina, ustilaginomycotine, agaricomycotina, and combinations thereof. In a preferred embodiment, the yeast is *Saccharomyces cervevisia*. In another preferred embodiment, the yeast is *Sacchromycetes boulardii*.

In a further embodiment of the invention, the yeast component is provided as whole cells, hydrolysate (i.e. hyrolyzed yeast extract, also called yeast peptone), autolyzed yeast, or as a desired component extract. In an exemplary embodiment, the yeast component can be a commercially available product. Commercially available yeast components include Celmanax, produced by Arm & Hammer Animal Nutrition.

The compositions according to the invention are superior to commercially-available yeasts products often included in probiotic compositions which only have Fructo Oligo Saccharides (FOS) which are derived from plants and as such are susceptible to stomach acids and denatured in the gut rendering them less effective. The compositions according to the invention overcome this shortcoming by including Mannan Oligo Saccharides (MOS) derived from the Yeast Cell Wall which are not denatured by stomach acids and thereby pass through the stomach and remain intact to proceed into the intestines where their benefits are derived according to the methods of the invention.

In an aspect of the invention, the composition provides from about 0.1 gram to about 0.5 grams of the prebiotic yeast in a 1 gram dosage, or from about 0.25 grams to about 0.5 grams of the prebiotic yeast in a 1 gram dosage.

Probiotic Component

Probiotics are live microorganisms which provide health benefits when consumed by potentially decreasing the number of potentially pathogenic microorganisms, strengthening the immune system, and increasing the number of beneficial flora in the digestive system. In an embodiment of the invention, a single probiotic strain is included in the dietary supplement composition. In a preferred embodiment of the invention, a combination of probiotic strains is included in the dietary supplement composition.

As referred to herein a "probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human, companion animal or livestock. Some species, strains, and/or subtypes of non-pathogenic bacteria and yeast are currently recognized as probiotics. Examples of probiotics include, but are not limited to, *Candida* spp., *Debaryomyces* spp., *Debaryomyces* spp., *Kluyveromyces* spp., *Kluyveromyces* spp., *Saccharomyces* spp., *Yarrowia* spp., *Bifidobacteria* spp., *Escherichia coli*, and *Lactobacillus* spp., e.g., *Candida humilis*, *Debaryomyces hansenii*, *Debaryomyces occidentalis*, *Kluyveromyces lactis*, *Kluyveromyces lodderae*, *Kluyveromyces marxianus*, *Saccharomyces cerevisiae*, *Saccharomyces boulardii*, *Yarrowia hpolytica*, *Bifidobacterium bifidum*, *Enterococcus faecium*, *Escherichia coli* strain *Nissle*, *Lactobacillus acidophilus*, *Lactobacillus bulgaricus*, *Lactobacillus paracasei*, and *Lactobacillus plantarum* (Dinleyici et al., 2014; U.S. Pat. No. 5,589,168; U.S. Pat. No. 6,203,797; U.S. Pat. No. 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria and/or yeast may be genetically engineered to enhance or improve probiotic properties.

In an exemplary embodiment, a probiotic strain can be selected from the phylum Lactobacilli, Bifidobacteria, Streptococcus, Enterococcus, Bacillus, and combinations thereof. In an embodiment of the invention the probiotic strain can be *Lactobacillus acidophilus*, *Lactobacillus brevis*, *Lactobacillus bulgaricus*, *Lactobacillus plantarum*, *Lactobacillus rhamnosus*, *Lactobacillus fermentum*, *Lactobacillus caucasicus*, *Lactobacillus helveticus*, *Lactobacillus lactis*, *Lactobacillus reuteri*, *Lactobacillus casei*, *Lactobacillus paracasei*, *Bifidobacterium bifidum*, *Bifidobacterium infantis*, *Bifidobacterium longum*, *Streptococcus thermophiles*, *Streptococcus cremoris*, *Streptococcus faeciurn*, *Streptococcus infantis*, *Enterococcus faecium*, *Bacillus subtilis*, and combinations thereof.

In an aspect of the invention, the composition provides at least one, at least two, at least three, at least four, at least five, or more probiotic strains. In an aspect, the probiotic component provides strains comprising at least one, at least two, at least three, or at least four strains comprising *Lactobacilli*, *Enterococcus*, and/or *Bacillus*. In a preferred embodiment, the probiotic component comprises *Enterococcus faecium*, *Bacillus subtilis*, *Lactobacillus acidophilus*, and *Lactobacillus casei*.

In an aspect of the invention, the composition provides from about $1 \times 10^7$ cfu and $1 \times 10^{10}$ cfu of the probiotic component in a 1 gram dosage, preferably about $1 \times 10^8$ cfu and $1\times10^9$ cfu of the probiotics in a 1 gram dosage, or more preferably $1\times10^9$ cfu of the probiotics in a 1 gram dosage.

Methods of Manufacture

In another aspect, the present invention involves methods of manufacturing a dietary supplement, namely a PPA neutraceutical composition according to the compositions disclosed herein.

According to an aspect of the invention, a dietary supplement is manufactured by obtaining at least two of the following components: an immune effector protein component, a prebiotic hydrolyzed yeast or yeast-based extract component, and a probiotic component. In some embodiments of the invention, the immune effector protein is obtained from chicken egg yolks. In a further embodiment of the invention, a hydrolyzed yeast or yeast-based extract is obtained as a commercial product, through culture methods, or as a by-product of fermentation processes. Probiotic strains can be obtained as commercial products.

Each of the components can be then mixed in a proportion to achieve the desired treatment effect based on animal species and disease and health concerns. According to an embodiment of the invention, a composition may contain at least two of the specified components. In a preferred embodiment of the invention, a composition contains all three of the specified components. In one aspect, components can be mixed in equal proportions.

According to an aspect of the invention, the components are provided in liquid or suspension and mixed to form a liquid or suspension composition. Alternatively, the components are provided in liquid or suspension form and dried to form a solid composition which may be pressed or shaped. It is to be understood that in achieving a final solid composition, other components to increase shape stability can be added. Such components include binders and similar components known in the art. In one aspect, the components of the compositions can be mixed in equal proportions.

In another aspect, the compositions of the present invention can be produced by combining the components in various proportions. For example, in compositions comprising two components, the two components can be combined in a 1:1 ratio. In compositions comprising three components, the three components can be combined in a 1:1:1 ratio. In another aspect, the components can be combined in unequal proportions. By way of non-limiting example, in compositions comprising two components, the two components can be combined in ratios between 10:1 and 1:10, including all ratios in between. In compositions comprising three components, the components can be combined in ratios ranging from 1:1:10-1:10:10-10:10:1-10:1:1 and all ratios in between. Other ratios may also be utilized.

Methods of Treatment

In another aspect, the present invention involves methods of treatment of animals by administering the compositions, i.e., dietary supplement and additives of the present invention. In one aspect, animals can be humans, livestock, and companion animals. It is to be understood that the compositions can be provided alone or mixed into food. It is also to be understood that each of the components of the desired composition can be administered simultaneously or in sequence. The compositions can be provided as a solid, liquid, or suspension. For example, the compositions may be administered at a standardized dose of 1 mL per 5 lbs to about 10 lbs of body weight.

In one aspect, the methods of treatment involve administration of a therapeutically effective amount of a composition as described herein. A "therapeutically effective amount" means the amount of the composition that will elicit the biological or medical response of a subject in need thereof that is being sought by the researcher, veterinarian, medical doctor or other clinician. In some embodiments, the subject in need thereof is a human. In certain embodiments, the mammal is a livestock or companion animal. In other embodiments, the mammal is human. Effective amounts of the compound may be determined by one of ordinary skill in the art but will vary depending on the compound employed, frequency of application and desired result, and will generally range from about 0.0000001% to about 50%, by weight, of the composition, preferably from about 0.001% to about 50%, by weight, of total composition, more preferably from about 0.001% to about 30%, by weight of the composition. In certain embodiments, the compound is about 0.004% by weight of the composition.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day. Compositions will include an effective amount of one or more antibodies of the invention and/or a polypeptide comprising an epitope that binds an antibody of the invention i.e. an amount that is sufficient to treat, ameliorate, or prevent a targeted disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. The compositions and methods of treating using the same can be used to target and treat various diseases or conditions to provide therapeutic effects. Such therapeutic effects can be measured and detected by various means well known in the art to confirm efficacy. These include for example, Abdominal Radiographs, Ultrasound, Fecal Analysis, Colonoscopies, Gastroscopy, Blood work (including Complete Blood Counts and Blood Chemistries), and the like in order to determine therapeutic efficacy of the compositions.

In an aspect of the invention, therapeutic efficacy can be measured by various parameters. For example, Coccidiosis (e.g. in cats and dogs) is diagnosed by detection of the Protozoal organisms in the stools when a Fecal Analysis is performed. Symptoms of Coccidiosis include watery diarrhea accompanied by blood and mucus in some instances due to an invasion of the Intestinal Mucosa by the organism which causes sloughing and bleeding and interferes with the natural absorption process which then results in diarrhea. In an aspect, the therapeutic efficacy of the compositions for treating Coccidia include, for example: Stools firming without the presence of blood and mucus; fecal analysis without the presence of offending organisms (i.e. negative for Coccidia).

In an aspect of the invention, therapeutic efficacy for treating Inflammatory Bowel Disease (IBD) can be measured by the amelioration or treatment of the characteristic symptoms of vomiting and chronic diarrhea. IBD is inflammation and results in degrees of thickening of the mucosal lining of the Gastrointestinal tract, with diagnostic tests including for example: Blood work (including complete blood count showing Anemia (i.e. decrease in the Red Blood Cells and/or Hemoglobin and often elevation in the White Blood Cell (WBC) count; abnormal levels of Proteins or Liver enzymes; Barium Contrast studies (where barium is given orally and as it is passing through the gastrointestinal tract intestinal wall abnormalities like increased thickness may be detected); ultrasound to detect and determine changes in the Intestinal wall; and tissue biopsy of a small portion of the intestines. In an aspect, the therapeutic efficacy of the compositions for treating IBD include, for example: firming of stools, biopsy showing improvements in Mucosal lining (e.g. decrease in inflammation and healthier mucosal tissues).

These and other measurements of therapeutic efficacy of the compositions can be employed to confirm, demonstrate and indicate treatment employing the compositions in a subject according to the various embodiments of the invention.

The compositions described herein may be administered at least in the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.0001 mg/kg/day to about 100 mg/kg/day or about 0.01 mg/kg/day to about 100 mg/kg/day. However, the actual amount of the compound to be administered in any given case will be determined by a physician taking into account the relevant circumstances, such as the age and weight of a patient, patient's general physical condition, and route of administration. In some instances, dosing is evaluated on a case-by-case basis.

In an exemplary embodiment, a dietary supplement composition is dosed in a paste at between about 0.5 to 2 mL per 10 pounds of body weight per day, wherein the composition comprises per 1 mL from about 0.1-0.5 grams of the prebiotic, between about 0.1-0.5 grams of the immune effector protein component, and between about $1 \times 10^7$ cfu and $1 \times 10^{10}$ cfu of the probiotics, preferably about $1 \times 10^8$ cfu and $1 \times 10^9$ cfu of the probiotics, or more preferably $1 \times 10^9$ cfu of the probiotics. In a further embodiment the probiotics comprise from about 30-60% *Enterococcus faecium*, 20-40% *Bacillus subtilis*, 5-15% *Lactobacillus acidophilus*, and 10-20% *Lactobacillus casei*. In a still further embodiment the probiotics comprise about 50% *Enterococcus faecium*, 30% *Bacillus subtilis*, 10% *Lactobacillus acidophilus*, and 10% *Lactobacillus casei*.

In a further exemplary embodiment, a dietary supplement composition is dosed as a powder at between about 0.5 grams to 1 gram per 20-50 pounds of body weight per day, wherein the composition comprises per 1 gram from about 0.1-0.5 grams of the prebiotic, between about 0.1-0.5 grams of the immune effector protein component, and between about $1.5 \times 10^7$ cfu and $2 \times 10^{10}$ cfu of the probiotics, and optionally from about 0.25 to about 0.5 grams yeast. In a further embodiment the probiotics comprise from about 30-60% *Enterococcus faecium*, 20-40% *Bacillus subtilis*, 5-15% *Lactobacillus acidophilus*, and 10-20% *Lactobacillus casei*. In a still further embodiment the probiotics comprise about 50% *Enterococcus faecium*, 30% *Bacillus subtilis*, 10% *Lactobacillus acidophilus*, and 10% *Lactobacillus casei*.

In a further aspect, treatment may be accomplished by providing components as a single composition, or by providing at least one component in a sequential manner. For example, a composition comprising a probiotic component and a yeast component can be administered before or after an immune effector protein component. The combined or sequentially provided components can be provided in equal doses or as effective amounts of each component.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: Mitigation of the Adverse Effects of Parvo Viral Enteritis in Dogs 11 dogs, ages 6 to 15 weeks, were treated using an exemplary composition according to an embodiment of the present invention. The exemplary composition (IG) comprises Celmanax hydrolyzed yeast and yeast-based extract, Globimax egg protein, and a probiotic component composed of *Enterococcus faecium, Bacillus subtilis, Lactobacillus acidophilus*, and *Lactobacillus casei*. All dogs were treated orally with IG at a standardized dose of 1 ml per 5 lbs of body weight. The 1 mL dosage contains 0.5 grams of the prebiotic yeast, 0.5 grams of the immune effector protein component, and $1 \times 10^9$ cfu of the probiotics (50% *Enterococcus faecium*, 30% *Bacillus subtilis*, 10% *Lactobacillus acidophilus*, and 10% *Lactobacillus casei*). Treatments performed in the mornings and only once daily. Symptoms and/or response was be recorded 3 times daily: AM-NOON—PM. Treatments were carried out for 5-7 days. Results are provided in Table 1, below. Animals with an asterisk before their name were given IG, antibiotics & fluid therapy. Animals without an asterisk were given antibiotics, fluids, colloidal silver and probiotic yogurt. Antibiotics/medication: M—Metoclopramide, G—Gentamycin, A—Amoxicillin, Z—Zantac.

TABLE 1

| NAME/TAG # | AGE (Weeks) | SEX | BREED | WEIGHT (Lbs) | VACCINATIO | DIARRHEA | VOMITING | DEHYDRATION (%) | CONDITION | MEDICATION | FLUIDS | DRINKING | EATING |
|---|---|---|---|---|---|---|---|---|---|---|---|---|---|
| *Onyx | 15 | F | Rott X Pitbull | 20.4 | 3 | Severe & Bloody | Yes | 5-6 | Fair | A, G, M, Z | Yes | Yes | No |
| *Blaze | 15 | F | Rott X Pitbull | 20.12 | 3 | Severe & Bloody | Yes | 6-8 | Fair | A, G, M, Z | Yes | Yes | No |
| *Magic | 15 | M | Rott X Pitbull | 22.2 | 3 | Severe & Bloody | Yes | 10-12 | Poor | A, G, M, Z | Yes | No | No |

TABLE 1-continued

| NAME/ TAG # | AGE (Weeks) | SEX | BREED | WEIGHT (Lbs) | VACCINATIO | DIAR- RHEA | VOM- ITING | DEHY- DRA- TION (%) | CON DITION | MEDI- CATION | FLU- IDS | DRINK- ING | EATING |
|---|---|---|---|---|---|---|---|---|---|---|---|---|---|
| *Nero | 15 | M | Rott X Pitbull | 21.8 | 3 | Severe & Bloody | Yes | 10-12 | Poor | A, G, M, Z | Yes | No | No |
| Boss | 15 | M | Rott X Pitbull | 21.8 | 3 | Severe & Bloody | Yes | 5-6 | Fair | A, G, M, Z | Yes | Yes | No |
| Soca | 15 | F | Rott X Pitbull | 19.6 | 3 | Severe & Bloody | Yes | 5-6 | Fair | A, G, M, Z | Yes | Yes | No |
| Sierra | 15 | F | Rott X Pitbull | 18.10 | 3 | Severe & Bloody | Yes | 6-8 | Fair | A, G, M, Z | Yes | Yes | No |
| Radar | 15 | M | Rott X Pitbull | 18.6 | 3 | Severe & Bloody | Yes | 10-12 | Poor | A, G, M, Z | Yes | No | No |
| *Jazz | 15 | F | Rott X Pitbull | 22 | 3 | Severe & Bloody | Yes | 5-6 | Fair | A, G, M, Z | Yes | Yes | Yes - Picking |
| Roxy | 8 | M | Pitbull | 13.4 | 1 | Severe & Bloody | No | 5 | Fair/ Good | A, G, M, Z | No | Yes | No |
| Jade | 6 | F | Pitbull | 5.6 | Nil | Severe & Bloody | Yes | 10-12 | Poor | A, G, M, Z | Yes | No | No |

Animals treated with IG displayed much higher temperatures, ranging from 103-105° F., which became comparable to non IG pups by day four. IG pups initially did not show improvement until dosage was increased from 1 ml per 5 lbs body weight. After day 3 dosage was standard 5 ml three times daily.

Follow up on Rott×Pitbull pups showed that all were doing extremely well, putting on 4-6 lbs per week following discharge. Additional observations and comments are provided in Table 2, below.

TABLE 2

| NAME/ TAG # | OBSERVATIONS & COMMENTS |
|---|---|
| *Onyx | Significantly Higher temps recorded in * pups. Started IG trial @ 1 ml-5 lbs OID for 3/7. Parvo confirmed |
| *Blaze | On day 4 mega dose given × 5 pups –10 ml then 5 ml BID 4/7. Parvo confirmed |
| *Magic | Vomiting and bl. diarr output higher in * pups for first 3 days. Parvo confirmed |

TABLE 2-continued

| NAME/ TAG # | OBSERVATIONS & COMMENTS |
|---|---|
| *Nero | Nero died suddenly on Dec. 3, 2016 despite major improvement and appearing stable. Parvo confirmed |
| Boss | Parvo confirmed |
| Soca | Parvo confirmed |
| Sierra | Parvo confirmed |
| Radar | Parvo confirmed |
| *Jazz | Recovered within 4 days - Parvo confirmed |
| Roxy | Recovered and discharged Nov. 3, 2016. Parvo not confirmed |
| Jade | Died Oct. 3, 2016 Parvo not confirmed |

Example 2: Use of IG as Prophylaxis to Improve the General Health, Condition and Survival Rate Current mortality rates for pups, especially after surgery, is approximately 30-40%. To assess the ability of exemplary prebiotic compositions according to embodiments of the present invention (IG) to provide prophylactic benefits, puppies between 6 and 12 weeks old were treated with IG as described above. The results are provided in Table 3 below.

TABLE 3

| NAME/ TAG# | AGE (weeks) | SEX | BREED | WT | FECAL | DEWORMING | DIARR | VOMIT | APPETITE | BAR | CONDITION | S/N |
|---|---|---|---|---|---|---|---|---|---|---|---|---|
| #05930 | 8 | F | Mixed | 3 lbs 8 oz | POS- HOOKS | VALVOMEC | NO | NO | GOOD | YES | FAIR/ GOOD | Y - 29/03/16 |
| #05970 | 6-7 | M | Mixed | 2 lbs 8 oz | POS- TAPES | PRAZIVET | NO | NO | GOOD | YES | GOOD | Y - 09/04/16 |
| #05971 | 6-7 | F | Mixed | 2 lbs 12 oz | POS- TAPES | PRAZIVET | NO | NO | GOOD | YES | GOOD | Y - 23/03/16 |
| #05972 | 6-7 | F | Mixed | 2 lbs 12 oz | POS- TAPES | PRAZIVET | NO | NO | GOOD | YES | GOOD | Y - 04/04/16 |
| #05973 | 6-7 | M | Mixed | 2 lbs 14 oz | POS- TAPES | PRAZIVET | NO | NO | GOOD | YES | GOOD | Y - 23/03/16 |
| **#05962 | 8+ | M | Mixed | 6 lbs 3 oz | NEG | VALVOMEC | NO | NO | GOOD | YES | FAIR | N - Died 24/03 |
| #05927 | 10 | M | Shih Tsu X | 3 lbs 9 oz | POS- R & H | VALVOMEC | SOFT | NO | GOOD | YES | GOOD | Y - 29/03/16 |
| #05931 | 8 | F | Mixed | 3 lbs 3 oz | POS- HOOKS | VALVOMEC | NO | NO | GOOD | YES | FAIR/ GOOD | Y - 06/04/16 |
| #05964 | 10 | M | Mixed | 4 lbs 12 oz | POS- TAPES | PRAZIVET | NO | NO | GOOD | YES | GOOD | Y - 29/03/16 |
| #05910 | 10 | M | Mixed | 5 lbs 8 oz | POS- TAPES | PRAZIVET | NO | NO | GOOD | YES | GOOD | Y - 19/04/16 |
| #05909 | 10 | F | Mixed | 5 lbs | POS- TAPES | PRAZIVET | NO | NO | GOOD | YES | GOOD | Y - 19/04/16 |

TABLE 3-continued

| NAME/TAG# | AGE (weeks) | SEX | BREED | WT | FECAL | DEWORMING | DIARR | VOMIT | APPETITE | BAR | CONDITION | S/N |
|---|---|---|---|---|---|---|---|---|---|---|---|---|
| #05908 | 10 | M | Mixed | 6 lbs 1 oz | POS-TAPES | PRAZIVET | NO | NO | GOOD | YES | GOOD | Y - 19/04/16 |
| #05907 | 10 | F | Mixed | 5 lbs 12 ozs | POS-TAPES | PRAZIVET | NO | NO | GOOD | YES | GOOD | Y - 19/04/16 |
| #05969 | 11 | F | Mixed | 3 lbs 2 oz | NEG | VALVOMEC | NO | NO | GOOD | YES | GOOD | NO |
| #05968 | 6-7 | M | Pitbull X | 4 lbs 4 oz | POS-TAPES | PRAZIVET | NO | NO | GOOD | YES | GOOD | Y - 07/04/16 |
| #05985 | 8 | M | Mixed | 8 lbs | NEG | VALVOMEC | NO | NO | GOOD | YES | GOOD | Y - 14/03/16 |
| #05817 | 7 | F | Mixed | 3 lbs 8 oz | NEG | VALVOMEC | NO | NO | GOOD | YES | GOOD | Y - 13/03/16 |
| **#05906 | 8 | M | Mixed | 4 lbs 6 oz | NEG | VALVOMEC | YES | YES | FAIR | YES | FAIR/GOOD | Y - 09/04/16 |
| #05991 | 7 | M | Mixed | 6 lb | POS-HOOKS | VALVOMEC | NO | NO | GOOD | YES | GOOD | Y - 23/03/16 |
| #05992 | 7 | M | Mixed | 5 lbs 10 oz | POS-HOOKS | VALVOMEC | NO | NO | GOOD | YES | GOOD | Y - 24/03/16 |
| #05993 | 7 | F | Mixed | 5 lbs 4 oz | POS-HOOKS | VALVOMEC | NO | NO | GOOD | YES | GOOD | Y - 24/03/16 |
| #05994 | 7 | M | Mixed | 6 lbs 2 oz | POS-HOOKS | VALVOMEC | NO | NO | GOOD | YES | GOOD | Y - 30/03/16 |
| #06002 | 8 | M | Mixed | 3 lbs | POS-ROUND | VALVOMEC | NO | NO | GOOD | YES | GOOD | Y - 11/04/16 |
| #06013 | 7 | M | Mixed | 4 lbs 8 oz | POS-R & H | VALVOMEC | NO | NO | GOOD | YES | GOOD | NO |
| #06106 | 6 | M | Mixed | 3 lbs 12 oz | POS-COCCI | VALVOMEC | SL. SOFT | NO | GOOD | YES | GOOD | NO |
| #06105 | 6 | M | Mixed | 3 lbs 4 oz | POS-COCCI | VALVOMEC | SL. SOFT | NO | GOOD | YES | GOOD | NO |
| #06107 | 6 | F | Mixed | 3 lbs 12 oz | POS-COCCI | VALVOMEC | SL. SOFT | NO | GOOD | YES | GOOD | NO |
| #06024 | 7 | F | Mixed | 2 lbs 12 oz | NEG | VALVOMEC | NO | NO | GOOD | YES | GOOD | NO |
| #06111 | 8 | M | Mixed | 3 lbs 8 oz | NEG | VALVOMEC | NO | NO | GOOD | YES | GOOD | NO |
| #06112 | 8 | F | Mixed | 3 lbs | NEG | VALVOMEC | NO | NO | GOOD | YES | GOOD | NO |
| #06113 | 8 | F | Mixed | 3 lbs 2 oz | NEG | VALVOMEC | NO | NO | GOOD | YES | GOOD | NO |
| #06098 | 10 | M | Mixed | 4 lbs 2 oz | POS-TAPE | PRAZIVET | NO | NO | GOOD | YES | GOOD | NO |
| #05899 | 12 | F | Mixed | 11 lbs 3 oz | POS-ROUNDS | VALVOMEC | NO | NO | GOOD | YES | GOOD | Y - 17/03/16 |
| #06060 | 6 | F | Mixed | 3 lbs 4 oz | POS-ROUNDS | VALVOMEC | NO | NO | GOOD | YES | GOOD | Y - 04/04/16 |

N.B.
**VALVOMEC DE-WORMER IS A COMBINATION OF ALBENDAZOLE AND IVOMECTIN
***PUP AGES ARE ESTIMATED BASED ON THEIR TEETH. ALL PUPS ARE DE-WORMED UPON ARRIVAL AND USUALLY REQUIRE TREATMENT FOR FLEAS AND/OR TICKS
*** ANY PUPS THAT STARTED THE TRIAL BUT DIED/OR HAD TO BE PTS WITHIN 72 HOURS DUE TO SIGNS OF PARVO; HAVE NOT BEEN INCORPORATED INTO STUDY.
***** ALL SYMPTOMS ARE AS NOTED UPON ARRIVAL AND COVERS THEIR TIME AT THE JSPCA. PLEASE NOTE THE W/END OF 1ST-4TH APRIL, PUPS DID NOT RECEIVE IG RESULTING IN LOSS OF APPETITE AND DEPRESSION. ALL IMPROVED AFTER RETURNING ON IG AS WELL AS A COURSE OF BACTRIM SUSPENSION.

Additional observations are provided in Table 4 below.

TABLE 4

| NAME/TAG# | COMMENTS |
|---|---|
| #05930 | Went Home |
| #05970 | Went Home |
| #05971 | Went Home |
| #05972 | Went Home |
| #05973 | Went Home |
| **#05962 | Cause Unknown |
| #05927 | Went Home |
| #05931 | Went Home |
| #05964 | Went Home |
| #05910 | Sx before starting trials |
| #05909 | Sx before starting trials |
| #05908 | Sx before starting trials |
| #05907 | Sx before starting trials |
| #05969 | Adopted/awaitin SX |
| #05968 | Went Home |
| #05985 | Sx before trials collect 23/03 |
| #05817 | Sx before trials went home 04/04 |
| **#05906 | Died Dec. 4, 2016 - Was @ JSPCA for 3/52. Started V & D by Nov. 4, 2016 |
| #05991 | Went Home |
| #05992 | Went Home |
| #05993 | Went Home |
| #05994 | Went Home |
| #06002 | Went Home |
| #06013 | Loss of Appetite & depressed. Rx 06/04 Bactrim Susp OID 10/7 Sx scheduled |
| #06106 | Loss of Appetite & depressed. Rx 06/04 Bactrim Susp OID 10/7 Sx scheduled |
| #06105 | Loss of Appetite & depressed. Rx 06/04 Bactrim Susp OID 10/7 Sx scheduled |
| #06107 | Loss of Appetite & depressed. Rx 06/04 Bactrim Susp OID 10/7 Sx scheduled |

TABLE 4-continued

| NAME/TAG# | COMMENTS |
| --- | --- |
| #06024 | Awaiting Adoption |
| #06111 | Scheduled for Surgery |
| #06112 | Awaiting Adoption |
| #06113 | Awaiting Adoption |
| #06098 | Scheduled for Surgery |
| #05899 | Was adopted and returned. Awaiting Adoption |
| #06060 | Was adopted but not collected |

Example 3: Mitigation of the Adverse Effects of Coccidiosis in Cats

To assess the ability of exemplary prebiotic compositions according to an embodiment of the present invention to mitigate the adverse effects of coccidosis in cats, kittens were treated as described above. The study characteristics are provided in Table 5 below.

TABLE 5

| TAG # | AGE (weeks) | SEX | WEIGHT | TREATMENT | | | | |
| --- | --- | --- | --- | --- | --- | --- | --- | --- |
| 16940 | 10 | F | 2 lbs | 0.4 ml IG OID | | | | |
| 17042 | 5 | M | 14 ozs | 0.2 ml IG OID | | | | |
| 17098 | 8 | M | 1 lb 4 oz | 0.4 ml Bactrim OID 10/7 | | | | |
| 17006 | 8 | F | 1 lb 8 oz | 0.5 ml Bactrim OID 10/7 | | | | |
| 17005 | 8 | F | 1 lb 6 oz | 0.3 ml IG OID | | | | |
| 17007 | 8 | F | 1 lb 8 oz | 0.3 ml IG OID | | | | |
| 17178 | 10 | M | 2.4 lbs | Cocci & Rounds | Valvomec | Soft Stool | No vomit | Fair appetite | On IG for 12 Days |
| 17179 | 10 | F | 1.12 lbs | Cocci & Rounds | Valvomec | Soft Stool | No vomit | Fair appetite | On IG 18 days + Lidaprim for 7 days – still +ve 22/04 |

All kittens checked out positive for coccidiosis and had to be isolated for the trial. The first three days of the trial, the cases on conventional treatment responded slightly better that the IG cases. Cats on IG showed no further deterioration nor did there general condition improve. On the 4th day of treatment the IG cats dosage was increased to 1 ml TID. The 1 mL dosage contains 0.5 grams of the prebiotic yeast, 0.5 grams of the immune effector protein component, and 1×109 cfu of the probiotics (50% *Enterococcus faecium*, 30% *Bacillus subtilis*, 10% *Lactobacillus acidophilus*, and 10% *Lactobacillus casei*).

There was noticeable improvement in weight, appetite and general condition over the next few days. Throughout the trial IG cats remained active and alert. Tag #16940 after ten days on IG continued to test positive for Coccidia despite general improvement in her overall condition. She was placed on Albon for ten days and tested negative on day 7. All participants were de-wormed upon admission using either valvomec or prazivet. Tag #'s 17005-7 had ocular discharges and eventually had to be treated with Ciplox Eye Oint.

General response to IG by the cats was very good. Animals maintained excellent appetites and energy levels throughout the study. Mega dosages were well tolerated though kittens would pass green stool similar in colouring to the IG. No withdrawal issues have been noted.

Example 4: Treatment of a Ten Month Old Dog with Severe Gastro-Intestinal Upset

The patient was presented at an outpatient clinic vomiting and not eaten for two days. Body condition was very good, no internal or external parasites found upon examination and the animal was still bright, active and responsive. Temperature, clotting time and CRT were normal, he was microfilaria negative, on routine prophylaxis, immunization up to date, no abdominal pain or discomfort noted upon palpation. The animal was prescribed Sulfatrim.

The animal returned and was admitted the following day due to vomiting, hence unable to keep down the medication. Abdominal x-ray showed no blockage; a significant amount of stool was noted. The animal was prescribed Enrovet, Zantac, and Metoclopramide. On the following day the animal was depressed and vomiting. The animal was placed on I.V. fluids.

Four days later the animal was put under sedation to facilitate extensive examination. Upon palpation the patient experienced a severe bout of diarrhea. Permission was sought from the owner before prescribing IG for this animal.

The animal was diagnosed as having possible *clostridium* infection. Prescribed treatment was 20 ml IG twice daily. The 1 mL dosage contains 0.5 grams of the prebiotic yeast, 0.5 grams of the immune effector protein component, and $1 \times 10^9$ cfu of the probiotics (50% *Enterococcus faecium*, 30% *Bacillus subtilis*, 10% *Lactobacillus acidophilus*, and 10% *Lactobacillus casei*). Upon examination following two days treatment the animal was more alert and responsive. The animal was also taking small amounts of fluid and food by mouth, and no vomiting was observed.

The following day I.V. fluids were withdrawn. The patient's appetite was much improved, and the patient was bright, alert, and responsive. Thereafter the patient passed small amount of formed stool, and was eating and drinking well with no vomiting. Patient was discharged.

Example 5: Use of IG as a Prophylaxis to Improve the General Health, Condition and Survival Rate of Kittens Mortality rates in felines are high especially after surgery. Treatment using an exemplary composition according to an embodiment of the present invention (IG) was investigated for the ability to help improve resistance to coccidiosis.

Kittens between 6 and 12 weeks old were treated as described above. The results are provided in Table 6 below.

TABLE 6

| NAME/TAG# | AGE (weeks) | SEX | WT. (lbs) | FECAL | DEWORMING | DIARR | VOMITING | APPETITE | BAR | CONDITION | S/N |
|---|---|---|---|---|---|---|---|---|---|---|---|
| 17166 | 6 | M | 1.2 | Neg | Valvomec | Soft Stool | No | Fair | Yes | Fair | No - PTS |
| 17167 | 6 | F | 1.8 | Neg | Valvomec | Soft Stool | No | Fair | Yes | Fair | No - PTS |
| 17168 | 6 | M | 1.6 | Neg | Valvomec | Soft Stool | No | Fair | Yes | Fair | No - PTS |
| 17169 | 6 | F | 1.2 | Neg | Valvomec | Soft Stool | No | Fair | Yes | Fair | No - PTS |
| 17177 | 10 | F | 1.1 | Cocci & Rounds | Valvomec | Soft Stool | No | Fair | Yes | Fair | 23/04/16 |
| 17178 | 10 | M | 2.4 | Cocci & Rounds | Valvomec | Soft Stool | No | Fair | Yes | Fair | 26/04/16 |
| 17179 | 10 | F | 1.12 | Cocci & Rounds | Valvomec | Soft Stool | No | Fair | Yes | Fair | — |
| 17187 | 8 | F | 1.8 | Neg | Valvomec | No | No | Good | Yes | Good | No - PTS |
| 17188 | 8 | F | 1.6 | Neg | Valvomec | No | No | Good | Yes | Good | No - PTS |
| 17189 | 8 | F | 1.6 | Neg | Valvomec | No | No | Good | Yes | Good | No - PTS |
| 17190 | 8 | M | 1.10 | Neg | Valvomec | No | No | Good | Yes | Good | No - PTS |
| 17191 | 8 | F | 1.12 | Neg | Valvomec | No | No | Good | Yes | Good | No - PTS |
| 17194 | 6 | F | 1.4 | Round | Valvomec | No | No | Good | Yes | Good | No - PTS |
| 17195 | 6 | M | 1.4 | Round | Valvomec | No | No | Good | Yes | Good | No - PTS |
| 17196 | 6 | F | 1.2 | Round | Valvomec | No | No | Good | Yes | Good | No - PTS |
| 17197 | 6 | F | 1.4 | Round | Valvomec | No | No | Good | Yes | Good | No - PTS |
| 17198 | 6 | F | 1 | Round | Valvomec | No | No | Good | Yes | Good | No - PTS |
| 17204 | 8 | M | 1.8 | Neg | Valvomec | No | No | Good | Yes | Good | 20/04/16 |
| 17205 | 8 | F | 1.5 | Neg | Valvomec | No | No | Good | Yes | Good | 26/04/16 |
| 17211 | 6 | M | 1.4 | Neg | Pyrantel | No | No | Fair - Picky | Yes | Good | 19/04/16 |
| 17216 | 8 | M | 1.6 | Neg | Valvomec | No | No | Good | Yes | Good | 21/04/16 |
| 17217 | 8 | F | 1.4 | Neg | Valvomec | No | No | Good | Yes | Good | 28/04/16 |
| 17218 | 8 | F | 1.4 | Neg | Valvomec | No | No | Good | Yes | Good | 21/04/16 |
| 17219 | 8 | M | 1.8 | Neg | Valvomec | No | No | Good | Yes | Good | 23/04/16 |
| 17220 | 8 | F | 1.4 | Neg | Valvomec | No | No | Good | Yes | Good | 27/04/16 |
| 17224 | 6-8 | F | 1.4 | Round | Valvomec | No | No | Good | Yes | Good | 3/5/2016 |
| 17225 | 6-8 | F | 1.2 | Round | Valvomec | No | No | Good | Yes | Good | 28/04/16 |
| 17228 | 8 | F | 1.4 | Neg | Valvomec | No | No | Good | Yes | Good | 2/5/2016 |
| 17229 | 8 | M | 1.4 | Neg | Valvomec | No | No | Good | Yes | Good | 26/04/16 |
| 17232 | 6 | M | 1 | Neg | Valvomec | No | No | Good | Yes | Good | 27/04/16 |
| 17236 | 5 mo | F | 4.8 | Neg | Valvomec | No | No | Good | Yes | Good | 25/04/16 |
| 17237 | 5 Mo | F | 4.3 | Neg | Valvomec | No | No | Good | Yes | Good | 21/04/16 |
| 17241 | 6 | M | 1.7 | Round | Valvomec | No | No | Fair - Good | Yes | Good | 25/04/16 |
| 17242 | 6 | F | 1.4 | Round | Valvomec | No | No | Fair - Good | Yes | Good | 27/04/16 |
| 17243 | 6 | F | 1.8 | Round | Valvomec | No | No | Fair - Good | Yes | Good | — |
| 17244 | 6 | F | 1.4 | Round | Valvomec | No | No | Fair - Good | Yes | Good | 3/5/2016 |
| 17249 | 12 | M | 2.4 | Neg | Valvomec | No | No | Good | Yes | Good | 29/04/16 |
| 17255 | 8 | M | 1.8 | Round | Pyrantel | No | No | Good | Yes | Good | — |
| 17257 | 8 | F | 1.2 | Round | Pyrantel | No | No | Good | Yes | Good | 25/04/16 |
| 17260 | 6 | M | 1.4 | Neg | Valvomec | No | No | Good | Yes | Good | 4/5/2016 |
| 17261 | 6 | M | 1.2 | Neg | Vavomec | No | No | Good | Yes | Good | 2/5/2016 |
| 17262 | 6 | F | 1.4 | Neg | Valvomec | No | No | Good | Yes | Good | — |
| 17265 | 6 | F | 1.6 | Round | Valvomec | No | No | Good | Yes | Good | — |
| 17266 | 6 | M | 1.8 | Neg | Valvomec | No | No | Good | Yes | Good | 26/04/16 |

The female kitten bearing Tag #17243 arrived on April 20th, in good condition and passed its check-up. The animal was found on the morning of May 3rd looking very ill (Depressed, not lively and weepy eyes), and was sent to the clinic where it was euthanized by the attending veterinarian; cause unknown, no post mortem was done. On April 12th kittens with tag #'s 17177, -78 & -79 were found to be coccidiosis and round worm positive. The animals were moved into isolation and a mega dosage of 2 mls was administered to each kitten. Kittens #'s-77 & -78 were given the all clear and had surgery April 23rd & 26th respectively. Kitten #17179 was found to be still positive on 22 April and placed on Lidaprim suspension in addition to I.G. Additional observations are provided in Table 7 below.

TABLE 7

| NAME/TAG# | |
|---|---|
| 17166 | On I.G. for 3 Days - Was not adopted |
| 17167 | On I.G. for 3 Days - Was adopted and awaiting Sx |
| 17168 | On I.G. for 3 Days - Was adopted and awaitin Sx |
| 17169 | On I.G. for 3 Days - Was not adopted |
| 17177 | On IG only for 14 days until discharged - Isolated |
| 17178 | On IG only for 12 Days - Isolated |

TABLE 7-continued

| NAME/ TAG# | |
|---|---|
| 17179 | **On IG 18 days + Lidaprim for 7 days - was still +ve 22/04 - Isol/DIED - 28/04 |
| 17187 | On I.G. for 3 Days - Was not adopted |
| 17188 | On I.G. for 3 Days - Was not adopted |
| 17189 | On I.G. for 3 Days - Was not adopted |
| 17190 | On I.G. for 3 Days - Was adopted, awaiting Sx |
| 17191 | On I.G. for 3 Days - Was adopted, awaiting Sx |
| 17194 | On I.G. for 3 Days - Was not adopted |
| 17195 | On I.G. for 3 Days - Was adopted and awaiting Sx |
| 17196 | On I.G. for 3 Days - Was not adopted |
| 17197 | On I.G. for 3 Days - Was not adopted |
| 17198 | On I.G. for 3 Days - Was not adopted |
| 17204 | On I.G. for 9 days |
| 17205 | On I.G. for 15 days |
| 17211 | ***On I.G. for 5 days - Hand reared |
| 17216 | On I.G. for 7 days |
| 17217 | On I.G. for 15 days |
| 17218 | On I.G. for 9 days |
| 17219 | On I.G. for 9 days |
| 17220 | On I.G. for 11 days |
| 17224 | On I.G. 18 days - awaiting collection |
| 17225 | On I.G. 12 days |
| 17228 | ****On I.G. for 15 days - +ve for Cocci on 26/04 went on Rx Lidaprim. Dep Apr. 5, 2016 |
| 17229 | ****On I.G. for 15 days - Found to be +ve for Cocci after Sx. Went on Rx Lidaprim. Dep Mar. 5, 2016 |
| 17232 | On I.G. 9 days - Died! Did not come out of anaesthetic |
| 17236 | On IG 9 days |
| 17237 | On IG 5 days |
| 17241 | On IG 7 Days |
| 17242 | On IG 10 Days |
| 17243 | *IG 14 days - stopped 03/05 - PTS |
| 17244 | On IG 16 days |
| 17249 | On IG 9 Days not collected yet-going up for re-adoption. |
| 17255 | On IG 9 days + Not adopted yet |
| 17257 | On IG 6 Days |
| 17260 | On I.G. 13 days + not collected yet |
| 17261 | On I.G. 13 days + Not collected yet |
| 17262 | On I.G. 13 Days + not adopted yet |
| 17265 | On G.I.13 days Not adopted yet |
| 17266 | On G.I. 4 days |

Example 6: Parvo Case Study 2

P.C. Two (2) Great Dane/Mastiff mixed pups. One of each sex. Both pups had received their 3rd vaccination on the 6 Apr. 2016. Both pups had undergone shortly after an ear cropping procedure which was performed outside of the JSPCA by another veterinary surgeon as the procedure is unavailable at the Society.

On Friday April 15th, the female pup was brought into the JSPCA for poor appetite and "looking poorly". Saturday April 16th pup was admitted as deterioration was rapid due to severe vomiting and diarrhea. On Monday April 18th, male pup was brought in and admitted as he was displaying similar symptoms to litter mate. Both pups were put on IG.

Example 7: Chronic Diarrhea Case Study—Dog

A 7 yr old Golden Retriever presented for chronic diarrhea, soft stools for 5 years, with gross blood in stools when presented. The animal has a history of traveling to 5 different countries in the past 5 years, most recently the Cayman Islands.

Physical exam: dog was bright, alert & responsive; surprisingly good body condition. Blood work—normal; fecal parasite tech—negative; fecal smear showed a lot of motile rod forms; intestinal PCR sent out.

Pending lab results, dog was sent home with metronidazole (Flagyl) 500 mg BID and 250 TID based on a 1 ml per 5 pounds of body weight. The 1 mL dosage contains 0.5 grams of the prebiotic yeast, 0.5 grams of the immune effector protein component, and $1 \times 10^9$ cfu of the probiotics (50% *Enterococcus faecium*, 30% *Bacillus subtilis*, 10% *Lactobacillus acidophilus*, and 10% *Lactobacillus casei*). PCR results indicated *Cryptosporidium*, and dog started on: Azithromycin SID, for 3 weeks.

Follow-up, 1 wk: dog stools completely firm, but still had bright, red blood. The animal was sent to a specialist where a rectal polyp found, removed, and determined to be a cancerous growth. At a re-check, at 3 months the dog continues to take IG daily with beneficially results.

Example 8: Chronic Diarrhea Case Study—Cat

Case 1: 4 yr old Cat presented for diarrhea. The history on this cat: finicky eater, so owner changed food often. Physical exam identified no abnormalities, young healthy cat, a bit underweight. Fecal float—negative, NPS; fecal smear showed high fat content to stools. A tentative diagnosis of food sensitivity, or malabsorption was made. No further testing was completed due to owner financial decision. The animal was sent home IG composition TID. The 1 mL dosage contains 0.5 grams of the prebiotic yeast, 0.5 grams of the immune effector protein component, and $1 \times 10^9$ cfu of the probiotics (50% *Enterococcus faecium*, 30% *Bacillus subtilis*, 10% *Lactobacillus acidophilus*, and 10% *Lactobacillus casei*). Follow-up, 1 week: stools formed, owner very happy, cat continues to take IG daily.

Case 2: 8 week old Kitten presented for diarrhea. The history on this kitten: owner acquired from rescue group. Physical exam: young, healthy kitten with irritated anal area. TPR—normal; Fecal float—positive for coccidia; fecal smear—positive for coccidia. Due to elderly owner's limitations with medication administration, kitten was treated at clinic with: Albon (pharmaceutical for treating coccidiosis) 1/wk, for 3 consecutive weeks. The kitten sent home with: IG TID. The 1 mL dosage contains 0.5 grams of the prebiotic yeast, 0.5 grams of the immune effector protein component, and $1 \times 10^9$ cfu of the probiotics (50% *Enterococcus faecium*, 30% *Bacillus subtilis*, 10% *Lactobacillus acidophilus*, and 10% *Lactobacillus casei*).

Follow-up, Wk 1 (during 2nd Albon admin): stools firm. Decreased IG to SID. Wk 3 (during final Albon admin): fecal float recheck—no coccidia found; kitten continues IG daily.

Example 9: Additional Dog Studies Case 1

12 yr old Yorki mix dog with congestive heart failure (CHF) presented for diarrhea. The history on this dog: owner uses different treats/foods to administer medications for CHF, due to difficulty in administration, as dog bites. Physical exam: All normal, except grade 4 heart murmur; mild respiratory lung sounds; stools very soft, no blood seen in stools; fecal float—NPS; fecal smear—4+ rods. The dog was treated with Famotidine, 1 inj. And dog sent home with: IG TID, until stools formed; then SID.

Follow-up, 1 week: normal stools, despite owner's continued use of multi treats/foods for CHF med administration. Owner observed complete restoration to normal stool in dog.

Case 2: 4 month old 50 lb Great Dane puppy presented for diarrhea. The history of this dog: Great Dane puppy ate everything in site, including owner's couch. Physical exam: BAR—no vomiting; GI palpated normally; fecal float NPS; fecal smear—4+ motile bacteria forms unidentified. Dog sent home with: Flagyl 500 mg SID, for 10 days, IG TID, until stools formed, then SID. Follow-up, 1 wk: hard stools, puppy continues to take IG daily. Puppy continues to eat everything in site.

What is claimed is:

1. A dietary supplement comprising:
   a prebiotic yeast component derived from a yeast cell wall, wherein said prebiotic yeast component comprises beta glucans, mannar oligosaccharides, mannose and/or galactosamine:
   an immune effector protein component comprising immunoglobulin Y;
   a probiotic component comprising Enterococcus faecium, Bacillus subtilis, Lactobacillus acidophilus, and Lactobacillus casei; and
   an inert diluent or an edible carrier, wherein the dietary supplement composition is in the form of a powder, paste, granule, capsule, tablet, bead, lozenge, gummy, suppository, suspension, emulsion, cream or liquid, wherein the prebiotic yeast component is present in an amount of from about 0.1 grams to about 0.5 grams, the immune effector protein component is present in an amount of from about 0.1 grams to about 0.5 grams, and the probiotic component is present in an amount of from about $1\times10^7$ cfu to about $1\times10^{10}$ cfu per each 1 gram or 1 ml of the dietary supplement.

2. The dietary supplement of claim 1, wherein the prebiotic yeast component is from a hydrolyzed yeast or yeast-based extract.

3. The dietary supplement of claim 1, wherein the prebiotic yeast component comprises beta glucans.

4. The dietary supplement of claim 1, wherein the immunoglobublin Y is from eggs.

5. The dietary supplement of claim 1, wherein the probiotic component is present in an amount of from about $1\times10^8$ dump out $1\times10^9$ cfu.

* * * * *

UNITED STATES PATENT AND TRADEMARK OFFICE
CERTIFICATE OF CORRECTION

PATENT NO. : 11,197,902 B2
APPLICATION NO. : 15/631422
DATED : December 14, 2021
INVENTOR(S) : Valentino Grant, Dayna J. Campbell and George D. Ranglin It is certified that error appears in the above-identified patent and that said Letters Patent is hereby corrected as shown below:

In the Claims

Column 23, Claim 1, Lines 9 and 10:
DELETE "mannar"
INSERT --mannan--
DELETE ":"
INSERT --;--

Column 24, Claim 4, Line 14:
DELETE "immunoglobublin"
INSERT --immunoglobulin--

Column 24, Claim 5, Line 18:
DELETE "dump out"
INSERT --cfu to about--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*